United States Patent [19]

Bryant et al.

[11] Patent Number: 5,792,762

[45] Date of Patent: Aug. 11, 1998

[54] DIHYDROBENZOFLUORENE COMPOUNDS, INTERMEDIATES, COMPOSITIONS AND METHODS

[75] Inventors: Henry Uhlman Bryant; Thomas Alan Crowell; Charles David Jones, all of Indianapolis, Ind.

[73] Assignee: Eli Lilly and Company, Indianapolis, Ind.

[21] Appl. No.: 933,801

[22] Filed: Sep. 19, 1997

Related U.S. Application Data

[60] Provisional application No. 60/026,755 Sep. 26, 1996.

[51] Int. Cl.$^6$ .................. A61K 31/40; A61K 31/445; C07D 207/08; C07D 211/22
[52] U.S. Cl. .................. 514/212; 514/239.5; 514/319; 514/428; 514/650; 540/609; 544/154; 546/195; 548/528; 558/57; 558/270; 558/271; 558/274; 560/108; 560/139; 564/322; 564/337; 564/338; 564/353; 564/354; 568/633; 568/719; 568/732
[58] Field of Search .................. 540/609; 544/154; 546/195; 548/528; 564/322, 337, 338, 353, 354; 514/212, 239.5, 319, 428, 650; 568/633, 719, 732

[56] References Cited

U.S. PATENT DOCUMENTS

| | | | |
|---|---|---|---|
| 3,274,213 | 9/1966 | Lednicer et al. | 548/576 |
| 3,394,125 | 7/1968 | Crenshaw | 548/525 |
| 3,413,305 | 11/1968 | Crenshaw | 548/525 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |

FOREIGN PATENT DOCUMENTS

| | | |
|---|---|---|
| 062 503 | 10/1982 | European Pat. Off. |
| WO 89/0289 | 4/1989 | WIPO . |
| WO 95/10513 | 4/1995 | WIPO . |

OTHER PUBLICATIONS

Crenshaw, R.R., et al. *J. Med. Chem.* 14(12):1185–1190 (1971).
Jones, C.D., et al. *J. Med. Chem.* 27: 1057–1066) 1984.
Jones, C.D., et al. *J. Med. Chem.* 35: 931–938 (1992).

*Primary Examiner*—Richard L. Raymond
*Attorney, Agent, or Firm*—Janelle D. Strode; David E. Boone

[57] ABSTRACT

The invention provides dihydronaphthofluorene compounds, formulations, and methods of inhibiting bone loss or bone resorption, particularly osteoporosis, and cardiovascular-related pathological conditions.

17 Claims, No Drawings

DIHYDROBENZOFLUORENE COMPOUNDS, INTERMEDIATES, COMPOSITIONS AND METHODS

BACKGROUND OF THE INVENTION

This application claims the benefit of U.S. Provisional Application No. 60/026,755, filed Sep. 26, 1996. Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients.

Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

In response to the clear need for new pharmaceutical agents which are capable of alleviating the symptoms of, inter alia, postmenopausal syndrome, the instant invention provides novel dihydrobenzofluorene compounds, pharmaceutical formulations thereof, and methods of using such compounds for the treatment of postmenopausal syndrome and other estrogen-related pathological conditions.

SUMMARY OF THE INVENTION

The instant invention relates to compounds of formula I:

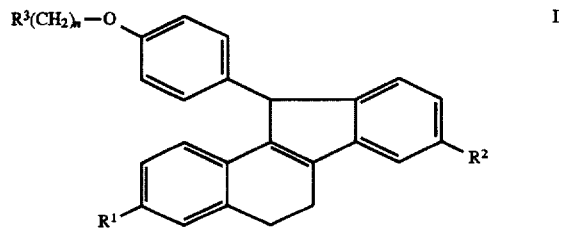

wherein:

$R^1$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, or —OSO$_2$($C_2$-$C_6$ alkyl);

$R^2$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, —OSO$_2$($C_2$-$C_6$ alkyl), or halo;

$R^3$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino; and n is 2 or 3;

or a pharmaceutically acceptable salt or solvate thereof.

The present invention further relates to intermediate compounds of formula II which are useful for preparing the pharmaceutically active compounds of the present invention, and are shown below

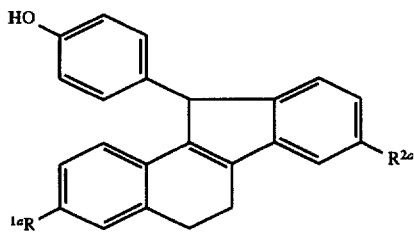

wherein:

$R^{1a}$ is —H or —$OR^5$ in which $R^5$ is a hydroxy protecting group.

and $R^{2a}$ is —H, halo, or —$OR^6$ in which $R^6$ is a hydroxy protecting group.

The instant invention still further relates to pharmaceutical formulations containing compounds of formula I, and the use of said compounds at least for the inhibition of bone loss or bone resorption, particularly osteoporosis and cardiovascular-related pathological conditions including hyperlipidemia.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, —$OC_1$–$C_4$ alkyls, and the like. Numerous reactions for the formation and removal of such protecting groups are described in a number of standard works including, for example, Protective Groups in Organic Chemistry, Plenum Press (London and New York, 1973); Green, T. W., Protective Groups in Organic Synthesis, Wiley, (New York, 1981); and The Peptides, Vol. I, Schrooder and Lubke, Academic Press (London and New York, 1965). Methods for removing preferred hydroxy protecting groups, particularly methyl and alkylsilyloxy, are essentially as described in the Examples, infra.

The term "solvate" represents an aggregate that comprises one or more molecules of the solute, such as a formula I compound, with one or more molecules of solvent.

The term "inhibit" includes its generally accepted meaning which includes prohibiting, preventing, restraining, and slowing, stopping, or reversing progression, severity, or ameliorating a resultant symptom or effect.

The term "leaving group" means a chemical entity which is capable of being displaced by an amino function via an $SN_2$ reaction. Such reactions are well known in the art and such groups would include halogens, mesylates, tosylates, and the like. A preferred leaving group would be bromo.

The compounds of formula I include:

3,8-dimethoxy-11-[4-[2-(1-piperidinyl)ethoxy]phenyl]-5,6-dihydro-11H-benzo[a]fluorene;

3,8-dihydroxy-11-[4-[2-(1-piperidinyl)ethoxy]phenyl]-5,6-dihydro-11H-benzo[a]fluorene;

3-hydroxy-8-methoxy-11-[4-[2-(1-piperidinyl)ethoxy]phenyl]-5,6-dihydro-11H-benzo[a]fluorene;

3-methoxy-8-hydroxy-11-[4-[2-(1-piperidinyl)ethoxy]phenyl]-5,6-dihydro-11H-benzo[a]fluorene;

3,8,9-trimethoxy-11-[4-[2-(1-piperidinyl)ethoxy]phenyl]-5,6-dihydro-11H-benzo[a]fluorene;

3,8,10-trimethoxy-11-[4-[2-(1-piperidinyl)ethoxy]phenyl]-5,6-dihydro-11H-benzo[a]fluorene;

9-fluoro-3,8-dimethoxy-11-[4-[2-(1-piperidinyl)ethoxy]phenyl]-5,6-dihydro-11H-benzo[a]fluorene;

9-chloro-3,8-dimethoxy-11-[4-[2-(1-piperidinyl)ethoxy]phenyl]-5,6-dihydro-11H-benzo[a]fluorene;

3,8-dimethoxy-9-methyl-11-[4-[2-(1-piperidinyl)ethoxy]phenyl]-5,6-dihydro-11H-benzo[a]fluorene;

3,8-dimethoxy-9-ethyl-11-[4-[2-(1-piperidinyl)ethoxy]phenyl]-5,6-dihydro-11H-benzo[a]fluorene;

8-methoxy-11-[4-[2-(1-piperidinyl)ethoxy]phenyl]-5,6-dihydro-11H-benzo[a]fluorene;

8-hydroxy-11-[4-[2-(1-piperidinyl)ethoxy]phenyl]-5,6-dihydro-11H-benzo[a]fluorene;

8,9-dimethoxy-11-[4-[2-(1-piperidinyl)ethoxy]phenyl]-5,6-dihydro-11H-benzo[a]fluorene;

8,10-dimethoxy-11-[4-[2-(1-piperidinyl)ethoxy]phenyl]-5,6-dihydro-11H-benzo[a]fluorene;

9-fluoro-8-methoxy-11-[4-[2-(1-piperidinyl)ethoxy]phenyl]-5,6-dihydro-11H-benzo[a]fluorene;

9-chloro-8-methoxy-11-[4-[2-(1-piperidinyl)ethoxy]phenyl]-5,6-dihydro-11H-benzo[a]fluorene;

8-methoxy-9-methyl-11-[4-[2-(1-piperidinyl)ethoxy]phenyl]-5,6-dihydro-11H-benzo[a]fluorene;

8-methoxy-9-ethyl-11-[4-[2-(1-piperidinyl)ethoxy]phenyl]-5,6-dihydro-11H-benzo[a]fluorene;

3,8-dimethoxy-11-[4-[2-(1-pyrrolidinyl)ethoxy]phenyl]-5,6-dihydro-11H-benzo[a]fluorene;

3,8-dihydroxy-11-[4-[2-(1-pyrrolidinyl)ethoxy]phenyl]-5,6-dihydro-11H-benzo[a]fluorene;

3-hydroxy-8-methoxy-11-[4-[2-(1-pyrrolidinyl)ethoxy]phenyl]-5,6-dihydro-11H-benzo[a]fluorene;

3-methoxy-8-hydroxy-11-[4-[2-(1-pyrrolidinyl)ethoxy]phenyl]-5,6-dihydro-11H-benzo[a]fluorene;

8-methoxy-11-[4-[2-(1-pyrrolidinyl)ethoxy]phenyl]-5,6-dihydro-11H-benzo[a]fluorene;

8-hydroxy-11-[4-[2-(1-pyrrolidinyl)ethoxy]phenyl]-5,6-dihydro-11H-benzo[a]fluorene;

8,9-dimethoxy-11-[4-[2-(1-pyrrolidinyl)ethoxy]phenyl]-5,6-dihydro-11H-benzo[a]fluorene;

8,10-dimethoxy-11-[4-[2-(1-pyrrolidinyl)ethoxy]phenyl]-5,6-dihydro-11H-benzo[a]fluorene;

3,8-dimethoxy-11-[4-[2-(1-methylpyrrolidinyl)ethoxy]phenyl]-5,6-dihydro-11H-benzo[a]fluorene;

3,8-dihydroxy-11-[4-[2-(1-hexamethyleneimino)ethoxy]phenyl]-5,6-dihydro-11H-benzo[a]fluorene;

3-hydroxy-8-methoxy-11-[4-[2-(1-morpholino)ethoxy]phenyl]-5,6-dihydro-11H-benzo[a]fluorene;

3-methoxy-8-hydroxy-11-[4-[2-(N,N-dimethylamino)ethoxy]phenyl]-5,6-dihydro-11H-benzo[a]fluorene;

3,8,9-trimethoxy-11-[4-[2-(N,N,-diethylamino)ethoxy]phenyl]-5,6-dihydro-11H-benzo[a]fluorene;

3,8,10-trimethoxy-11-[4-[2-(1-methylpyrrolidinyl)ethoxy]phenyl]-5,6-dihydro-11H-benzo[a]fluorene;

9-fluoro-3,8-dimethoxy-11-[4-[2-(N,N-dimethylamino)ethoxy]phenyl]-5,6-dihydro-11H-benzo[a]fluorene;

9-chloro-3,8-dimethoxy-11-[4-[2-(N,N-diisopropylamino) ethoxy]phenyl]-5,6-dihydro-11H-benzo[a]fluorene;

8-methoxy-11-[4-[2-(1-pyrrolidinyl)ethoxy]phenyl]-5,6-dihydro-11H-benzo[a]fluorene;

8-hydroxy-11-[4-[2-(1-methylpyrrolidinyl)ethoxy]phenyl]-5,6-dihydro-11H-benzo[a]fluorene;

8,9-dimethoxy-11-[4-[2-(1-methylpyrrolidinyl)ethoxy] phenyl]-5,6-dihydro-11H-benzo[a]fluorene;

8,10-dimethoxy-11-[4-[2-(1-methylpyrrolidinyl)ethoxy] phenyl]-5,6-dihydro-11H-benzo[a]fluorene, and the like.

The preferred embodiment of the current invention is 3,8-dimethoxy-11-[4-[2-(1-piperidinyl)ethoxy]phenyl]-5,6-dihydro-11H-benzo[a]fluorene.

The compounds of this invention are derivatives of benzofluorene, which is named and numbered according to the Ring Index, The American Chemical Society, as follows:

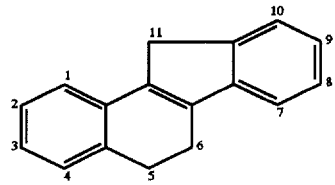

The starting material for preparing compounds of the present invention is a compound of formula III

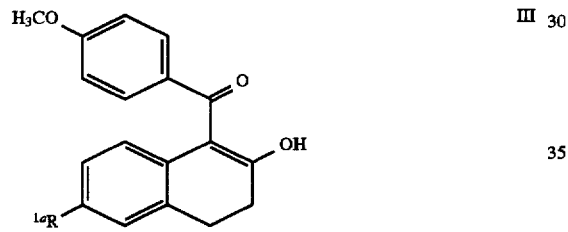

wherein $R^{1a}$ is —H or —OR$^5$ in which R$^5$ is a hydroxy protecting group; and $R^{2a}$ is —H, halo, or —OR$^6$ in which R$^6$ is a hydroxy protecting group.

Compounds of formula III are well known in the art and are prepared essentially as described by Jones et al. in U.S. Pat. No. 4,400,543 and Jones et al. in U.S. Pat. No. 5,147,880 the disclosures of which are herein incorporated by reference. See also, Jones et al., *J. Med. Chem.*, 35:931–8 (1992) and Jones et al., *J. Med. Chem.*, 22:962 (1979).

In preparing compounds of the present invention, generally, a 1-acylated-2-tetralone of formula III is treated with a base to form its corresponding anion, which is reacted with diphenylchlorophosphate, providing an enol phosphate derivative of formula IV. The formula IV compound undergoes formal addition-elimination when treated with an aryl Grignard reagent, which results in substitution of the 2-phosphate substituent by the aryl moiety, thereby producing a compound of formula V. Dealkylation of formula V compound by a thiolate anion demethylation reagent selectives dealkylates the group which is located para to the electron-withdrawing carbonyl group. The result of such selective dealkylation is a phenolic compound of formula VI, which can be reduced under the influence of hydride reducing agents to produce an allylic alcohol derivative of formula VII. The allylic alcohol is then cyclized under the influence of an acid catalyst to provide a benzofluorene derivative of formula II. A compound of formula II serves as an intermediate to the compounds of this invention. This synthetic route is as shown below in Scheme I, and $R^{1a}$ and $R^{2a}$ are as defined above.

Scheme I

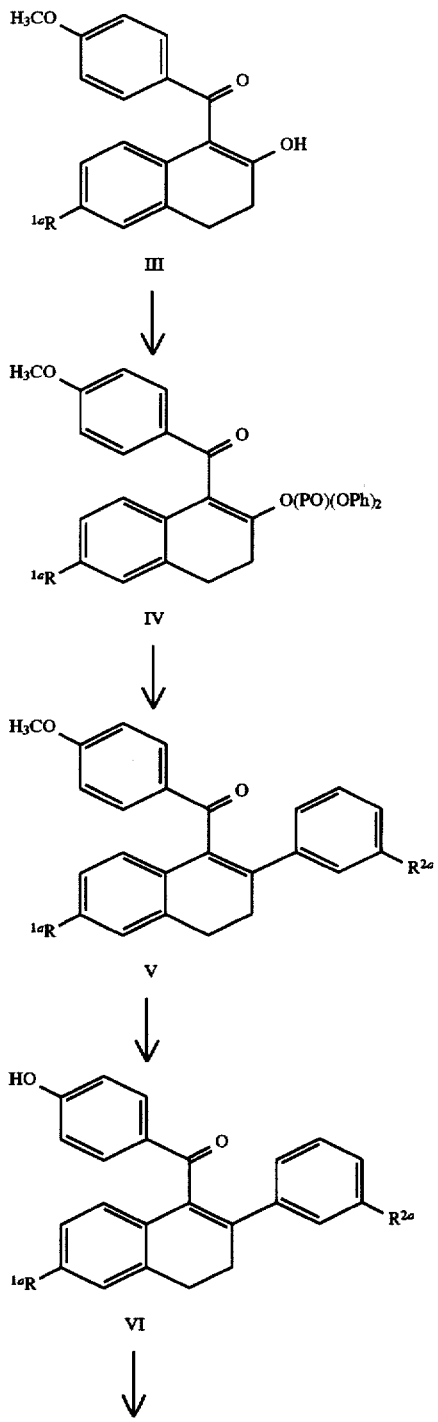

Scheme I
-continued

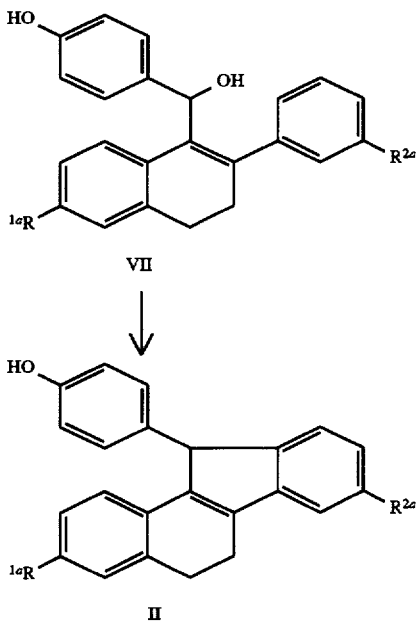

In the first step of the present process, a compound of formula III is converted to a dihydronaphthalene derivative of formula V via a two-step protocol, essentially as described by Jones et al., *J. Med. Chem.*, 35: 931–8 (1992). In essence, a formula III enolic compound is phosphorylated by one or more equivalents of a phosphorylating reagent which is a diarylchloro- or diarylbromo-phosphate and preferably diphenylchlorophosphate. This reaction may be carried out in a variety of inert solvents including ethers, THF, dioxane, ethyl acetate, toluene, and acetonitrile and in the presence of an acid scavenger such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature so as to avoid unwanted side products, elevated temperatures can also be used, but they are usually unnecessary to complete the phosphorylation reaction. The product of the phosphorylation reaction, an enol phosphate derivative of formula IV may be isolated by usual techniques, such as chromatography. However, it is most convenient to generate the enolphosphate using a solvent/acid scavenger combination which is compatable with the next step of the reaction (addition of a Grignard reagent). Thus, the combination of sodium hydride in THF under a nitrogen atmosphere is preferred, and provides a rapid phosphorylation leading to a compound of formula IV.

The intermediate enolphosphate, either isolated or generated in situ, may then be reacted with one or more equivalents of an aryl Grignard reagent or an aryl lithium organocuprate reagent. One to two equivalents of an aryl magnesium bromide is preferred, and phenyl magnesium bromide or 4-methoxyphenyl magnesium bromide is particularly preferred. The reaction is typically conducted at ice bath temperature to minimize side reactions, but elevated temperatures can be used to increase the rate of the reaction. The addition of the aryl moiety, followed by the elimination of the phosphate leaving group (formally an addition, elimination process) gives rise to a dihydronaphthalene derivative of formula V, which can be isolated by conventional techniques such as crystallization or chromatography.

The resulting dihydronaphthalene derivative of formula V is then demethylated to provide an intermediate of formula VI. In order to accomplish regioselective demethylation at the methoxy group para to the carbonyl, a nucleophilic demethylation reagent is used, and alkali metal thiolates (alkali metal salt of an organic thiol) are preferred. Especially preferred are lithium thioethylate or lithium thiomethylate, in excess to the extent of 1.2 or more equivalents of the demethylation reagent over the substrate. The reaction is conducted under an inert atmosphere to preserve the demethylation reagent and in a solvent which is practically inert to the nucleophilic nature of the thiolate reagent. Suitable solvents for the demethylation are those which are most conducive to bimolecular nucleophilic displacement reactions, and these include dimethylsulfoxide dimethylformamide, dimethylacetamide, and THF. Anhydrous dimethylformamide is preferred. In order to sumultaneously achieve a satisfactory reaction rate and also obtain good control of the selectivity for demethylation at the site para to the carbonyl group, it is important to carefully control the temperature of the reaction. Although the demethylation process will take place in the range of temperatures from 60° C. to 120° C., it is advantageous to use a temperature in the range of 80° to 90° C. to optimize the yield of the desired product. A temperature of 80° C. is particularly preferred. Under the preferred reaction conditions, the transformation from a formula V compound to a formula VI compound is complete after heating for about 2 to 4 hours at the indicated temperature.

A formula VI compound, or a salt thereof, is added to an appropriate solvent and reacted with a reducing agent such as, for example, lithium aluminum hydride (LAH).

The amount of reducing agent used in this reaction is an amount sufficient to reduce the carbonyl group of formula VI compound to form the carbinol compounds of formula VII. Generally, a liberal excess of the reducing agent per equivalent of the substrate is used.

Appropriate solvents include any solvent or mixture of solvents which will remain inert under reducing conditions. Suitable solvents include diethyl ether, dioxane, and tetrahydrofuran (THF). The anhydrous form of these solvents is preferred, and anhydrous THF is especially preferred.

The temperature employed in this step is that which is sufficient to effect completion of the reduction reaction, typically from 0° C. to 50° C. Ambient temperature, in the range of from about 17° C. to about 25° C., generally is adequate.

The length of time for this step is that amount necessary for the reaction to occur. Typically, this reaction takes from about 1 hour to about 20 hours. The optimal time can be determined by monitoring the progress of the reaction via conventional chromatographic techniques.

In the final transformation shown in Scheme I, the allylic alcohol derivative of formula VI undergoes a cyclization-dehydration process which produces the dihydrobenzofluorene derivative of formula II. This process is acid-catalyzed and a variety of mineral acids, Lewis acids, and organic acids stronger than acetic acid may be used. Among these catalysts are alkylsulfonic acids, arylsulfonic acids, sulfuric acid, hydrochloric acid, hydrobromic acid, polyphosphoric acid, and boron trifluoride etherate. Hydrochloric acid is preferred. The cyclization reaction typically proceeds at room temperature, but higher temperatures may be advantageous in speeding up the reaction rate.

Under the preferred reaction conditions, the transformation from a formula VII compound to a formula II compound is complete after stirring for about 5 minutes to about 2 hours at 50° C. temperature, or by stirring for overnight at ambient temperature.

Compounds of formula II are useful for the preparation of pharmaceutically active compounds of formula I of the present invention. The compounds of formula II include:

4-(3,8-dimethoxy-5,6-dihydro-11H-benzo[a]fluoren-11-yl)phenol;
4-(3,8,9-trimethoxy-5,6-dihydro-11H-benzo[a]fluoren-11-yl)phenol;
4-(3,8-10-trimethoxy-5,6-dihydro-11H-benzo[a]fluoren-11-yl)phenol;
4-(9-fluoro-3,8-dimethoxy-5,6-dihydro-11H-benzo[a]fluoren-11-yl)phenol;
4-(9-chloro-3,8-dimethoxy-5,6-dihydro-11H-benzo[a]fluoren-11-yl)phenol;
4-(3,8-dimethoxy-9-methyl-5,6-dihydro-11H-benzo[a]fluoren-11-yl)phenol;
4-(3,8-dimethoxy-9-ethyl-5,6-dihydro-11H-benzo[a]fluoren-11-yl)phenol;
4-(8-methoxy-5,6-dihydro-11H-benzo[a]fluoren-11-yl)phenol;
4-(8,9-dimethoxy-5,6-dihydro-11H-benzo[a]fluoren-11-yl)phenol;
4-(8,10-dimethoxy-5,6-dihydro-11H-benzo[a]fluoren-11-yl)phenol;
4-(9-fluoro-8-methoxy-5,6-dihydro-11H-benzo[a]fluoren-11-yl)phenol;
4-(9-chloro-8-methoxy-5,6-dihydro-11H-benzo[a]fluoren-11-yl)phenol;
4-(8-methoxy-9-methyl-5,6-dihydro-11H-benzo[a]fluoren-11-yl)phenol;
4-(8-methoxy-9-ethyl-5,6-dihydro-11H-benzo[a]fluoren-11-yl)phenol, and the like.

Upon preparation of a formula II compound, it is reacted with a compound of formula VIII $$R^3-(CH_2)_n-Q \qquad VIII$$

wherein $R^3$ and n are as defined above and Q is a bromo or, preferably, a chloro moiety, to form a compound of formula Ia. The formula Ia compound is then deprotected, when $R^5$ and/or $R^6$ hydroxy protecting groups are present, to form a compound of formula Ib. These process steps are shown in Scheme II below.

Scheme II

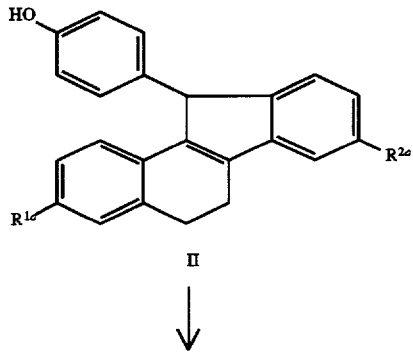

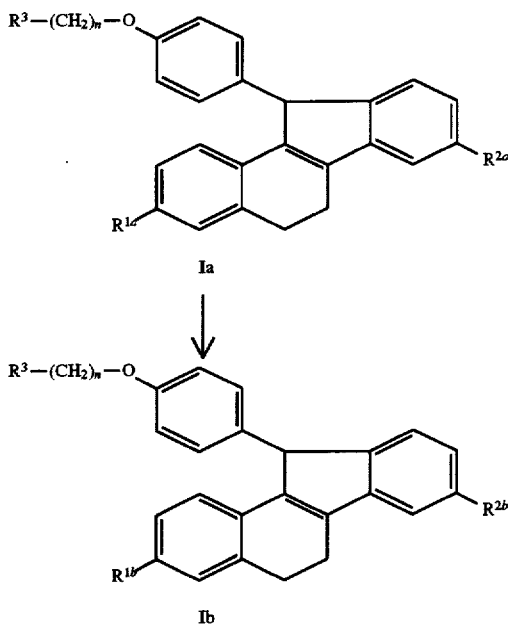

-continued
Scheme II wherein:
$R^{1a}$, $R^{2a}$, $R^3$, and n are as defined above;
$R^{1b}$ is —H or —OH; and
$R^{2b}$ is —H, —OH, or halo;
or a pharmaceutically acceptable salt thereof.

In the first step of the process shown above in Scheme II, the alkylation is carried out via standard procedures. Compounds of formula VIII are commercially available or are prepared by means well known to one of ordinary skill in the art. Preferably, the hydrochloride salt of a formula VIII compound, particularly 2-chloroethylpiperidine hydrochloride, is used.

Generally, at least about 1 equivalent of formula II substrate are reacted with 2 equivalents of a formula VIII compound in the presence of at least about 4 equivalents of an alkali metal carbonate, preferably cesium carbonate or potassium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Often, ambient temperature is sufficient and preferred, but in certain cases, higher temperatures may be required.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formula Ia, a formula II compound is reacted with an excess of an alkylating agent of the formula $$Q-(CH_2)_n-Q'$$

wherein Q and Q' each are the same or different leaving group, in an alkali solution. Appropriate leaving groups include the sulfonates such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methyethyl ketone (MEK) or DMF. In this solution, the 4-hydroxy group of the phenolic moiety of a formula II compound exists as a phenoxide ion which displaces one of the leaving groups of the alkylating agent.

This reaction is best when the alkali solution containing the reactants and reagents is brought to reflux and allowed to run to completion. When using MEK as the preferred solvent, reaction times run from about 6 hours to about 20 hours.

The reaction product from this step is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, or other secondary amines, via standard techniques, to form compounds of formula Ia. Preferably, the hydrochloride salt of piperidine is reacted with the alkylated compound of formula IIb in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

An alternative route for preparing compounds of the present invention is depicted in Scheme III, in which $R^{1a}$, $R^{2a}$ and $R^3$ are as defined above.

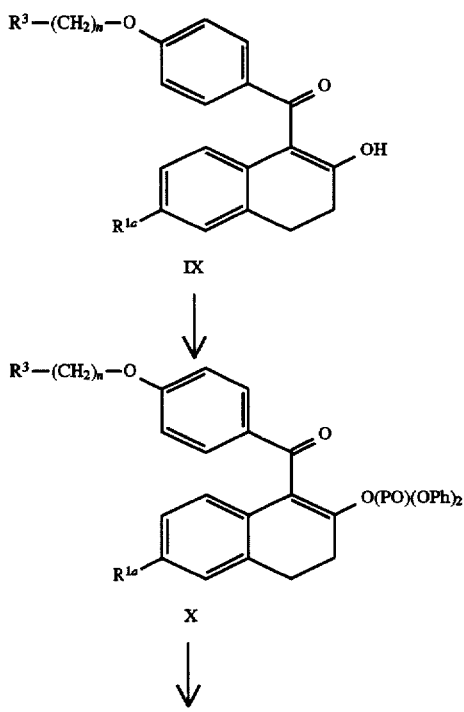

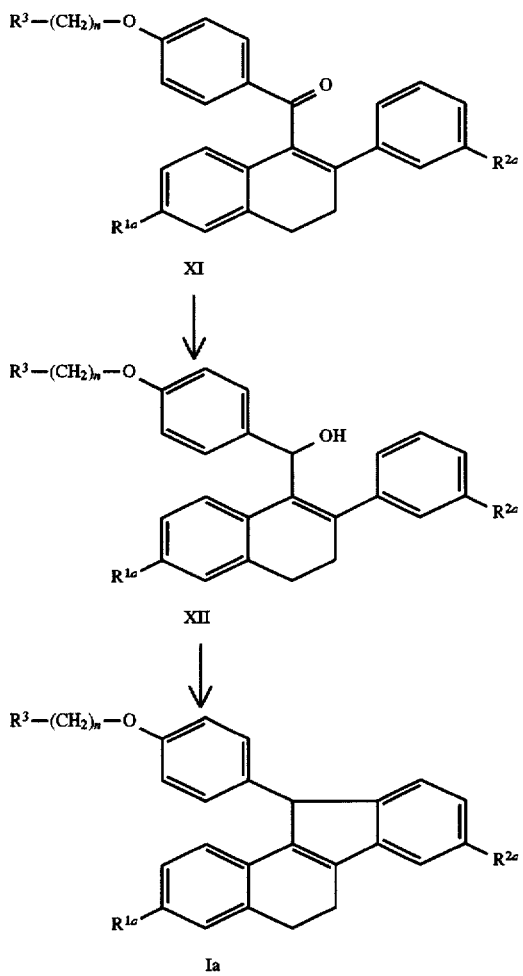

In this alternative, the starting material, a 1-acylated-2-tetralone of formula IX already includes the basic side chain moiety. The compound of formula IX treated with a base to form its corresponding anion, which is reacted with diphenylchlorophosphate, providing an enol phosphate derivative of formula X. The formula X compound undergoes formal addition-elimination when treated with an aryl Grignard reagent, which results in substitution of the 2-phosphate substituent by the aryl moiety, thereby producing a dihydronaphthalene compound of formula XI. Reduction of the carbonyl group to produce a benzylic alcohol of formula XII and subsequent cyclization under acidic conditions provides a formula Ia compound of this invention In essence, a formula IX enolic compound which already bears the basic side chain is phosphorylated by one or more equivalents of a phosphorylating reagent which is a diarylchloro- or diarylbromo-phosphate and preferably diphenylchlorophosphate. This reaction, may be carried out in a variety of inert solvents including ethers, THF, dioxane, ethyl acetate, toluene, and acetonitrile and in the presence of an acid scavenger such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature so as to avoid unwanted side products, elevated temperatures can also be used, but they are usually unnecessary to complete the phosphorylation reaction. The product of the phosphorylation reaction, an enol phosphate derivative of formula X may be isolated by usual techniques, such as chromatography. However, it is most convenient to generate the enolphosphate using a solvent/acid scavenger combination which is compatable with the next step of the reaction (additon of a Grignard reagent). Thus, the combination of sodium hydride in THF under a nitrogen atmosphere is preferred, and leads to a rapid phosphorylation leading to a compound of formula X.

The intermediate enol phosphate of formula X is either isolated or generated in situ, and is then reacted with one or more equivalents of an aryl Grignard reagent or an aryl lithium organocuprate reagent. One to two equivalents of an aryl magnesium bromide is preferred, and phenyl magnesium bromide or 4-methoxyphenyl magnesium bromide is particularly preferred. The reaction is typically conducted at ice bath temperature to minimize side reactions, but elevated temperatures can be used to increase the rate of the reaction. The addition of the aryl moiety, followed by the elimination of the phosphate leaving group (formally an addition, elimination process) gives rise directly to a dihydronaphthalene derivative of formula XI, which can be isolated by conventional techniques such as crystallization of the free base or salts or chromatography of the former.

The reduction of the carbonyl group of a compound of formula XI to the carbinol of formula XII is effected in the same manner as provided above for Scheme I.

In the final transformation shown in Scheme III above, the dihydronaphthalene derivative of formula X undergoes a cyclization-dehydration process which produces the dihydrobenzofluorene derivative of formula Ia. This process is acid-catalyzed and a variety of mineral acids, Lewis acids, and organic acids may be used. Among these catalysts are alkylsulfonic acids, aryl sulfonic acids, sulfuric acid, hydrochloric acid, hydrobromic acid, polyphosphoric acid, and boron trifluoride etherate. Hydrochloric acid is preferred. The cyclization reaction typically proceeds at room temperature, but higher temperatures may be advantageous in speeding up the reaction rate.

Under the preferred reaction conditions, the transformation from a formula XII compound to a formula Ia compound is complete after stirring for about 5 minutes to about 2 hours at 50° C. temperature or by stirring for overnight at ambient temperature.

Compounds of formula Ia, in which $R^5$ and/or $R^6$, when present, are $C_1-C_4$ alkyl, preferably methyl, are pharmaceutically active for the methods herein described. Accordingly, such compounds are encompassed by the definition herein of compounds of formula I.

Preferred compounds of formula I are obtained by cleaving, when present, the $R^5$ and $R^6$ hydroxy protecting groups of formula Ia compounds via well known procedures. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred $R^5$ and/or $R^6$ hydroxy protecting groups, particularly methyl, are essentially as described in the Examples, infra.

Compounds of formula Ia are pharmaceutically active for the methods herein described, and are encompassed by formula I as defined herein. Both isomers and mixtures of isomers generated at the 10-position are contemplated by, and within the scope of, the compounds of formula I.

Other preferred compounds of formula I are prepared by replacing the 3-position and/or 8-position hydroxy moieties, when present, with a moiety of the formula —O—CO—($C_1-C_6$ alkyl), or —O—$SO_2$—($C_2-C_6$ alkyl) via well known procedures. See, for example, U.S. Pat. No. 4,358,593.

For example, when an —O—CO($C_1-C_6$ alkyl) group is desired, a mono- or dihydroxy compound of formula I is reacted with an acylating agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., *Tetrahedron*, 36:2409–2433 (1980).

The present reactions are carried out at moderate temperatures, in the range from about –25° C. to about 100° C., frequently under an inert atmosphere such as nitrogen gas. However, ambient temperature is usually adequate for the reaction to run.

Acylation of a 3-position and/or 8-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, *Bull. Chem. Soc. Japan*, 38:1979 (1965), and *Chem. Ber.*, 788 and 2024 (1970).

Each of the above techniques which provide —O—CO—($C_1-C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the 3-position and/or 8-position hydroxy group of a formula I compound is converted to a group of the formula —O—$SO_2$—($C_2-C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting further symptoms in mammals, including humans, suffering from bone loss or bone resorption, particularly osteoporosis, and cardiovascular-related pathological conditions including hyperlipidemia, and related cardiovascular pathologies.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to inhibit the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof usually at least for thirty days, and more typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
| --- | --- |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

3,4-dihydro-1-(4-methoxybenzoyl)]-6-methoxy-2-naphthalenyl diphenyl phosphoric acid ester

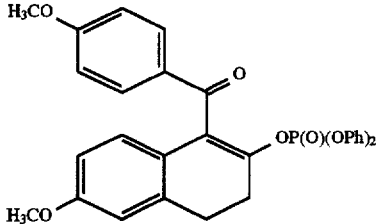

To a solution of 3,4-Dihydro-6-methoxy-1-(4-methoxybenzoyl)-2(1H)-naphthalenone (1.50 g, 0.0048 mol) at 5° C. under $N_2$ in 15 mL $CH_2Cl_2$ was added diphenylchlorophosphate (1.36 g, 0.0051 mol) and 4-dimethylaminopyridine (5 mg). Triethylamine (0.514 g, 0.0051 mol) in $CH_2Cl_2$ (20 mL) as then added dropwise over 10 min. while keeping the reaction temperature below 5° C. The resulting mixture was stirred overnight, and then it was poured over brine and ice and the crude product was extracted by EtOAc (50 mL). The organic layer was washed well with brine, dried over anhydrous $K_2CO_3$, and evaporated to obtain 2.92 g of a yellow oil. Silica gel chromatography which utilized 10% EtOAc in toluene gave the desired product as a yellow oil, 2.17 g (83%) This material gave a strong peak in its field desorption mass spectrum at M/e 542 and was essentially a single component by NMR spectroscopy. However, it failed to crystallize and did not give an acceptable combustion analysis for carbon. Anal. ($C_{31}H_{27}PO_7$) calcd C, 68.63; H, 5.02; O, 12.96. Found: C, 65.37; H, 4.89; O, 13.26.

$^1H$ NMR ($CDCl_3$) d 7.91 (d, J=8.8 Hz, 2H), 7.20–6.97 (m, 9H), 6.95–6.73 (m, 5H), 6.58 (dd, J=8.5 Hz, J=2.4 Hz, 1H), 3.83 (s, 3H), 3.75 (s, 3H), 3.07 (t, J=7.8 Hz, 2H), 2.88 (t, J=7.8 Hz, 2H); MS (FD) m/e 542 (M+).

Preparation 1A 3,4-dihydro-1-[4-[2-(1-piperidinyl)ethoxy]benzoyl)]-6-methoxy-2-naphthalenyl diphenyl phosphoric acid ester

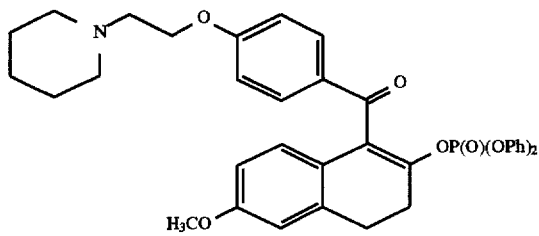

This compound was prepared in an analogous manner to the compound of Preparation 1. Appearance: dark yellow oil.

¹H NMR (CDCl₃) d 7.85 (d, J=8.7 Hz, 2H), 7.39–6.92 (m, 9H), 6.92–6.69 (m, 5H), 6.57 (dd, J=8.5 Hz, J=2.4 Hz, 1H), 4.03 (t, J=5.9 Hz, 2H), 3.77 (s, 3H), 3.07 (t, J=8.1 Hz, 2H), 2.89 (t, J=8.1 Hz, 2H), 2.78 (t, J=7.2, 2H), 2.62–2.42 (m, 4H), 1.77–1.55 (m, 4H), 1.55–1.37 (m, 2H); MS (FD) m/e 639 (M+).

Preparation 2

[3,4-dihydro-6-methoxy-2-(3-methoxyphenyl)-1-naphthalenyl](4-methoxyphenyl)methanone

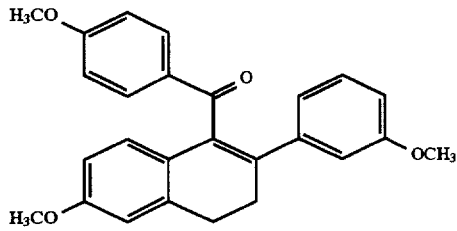

Sodium hydride (60% in mineral oil, 5.4 g, 0.135 mol) was suspended in anhydrous THF (80 mL) under a nitrogen atmosphere and the mixture was cooled to 5° C. in an ice bath. A solution consisting of 3,4-dihydro-6-methoxy-1-(4-methoxybenzoyl)-2(1H)-naphthalenone (38.0 g, 0.122 mol) and diphenyl chlorophosphate (36.3 g, 28.0 mL, 0.135 mol) in THF (150 mL) was added at a rate so that the temperature of the reaction mixture remained below 10° C. Following the initially rapid evolution of hydrogen gas, the reaction mixture was stirred for 2 hr with continued cooling from the ice bath. Analysis of a small sample by TLC (SiO₂, Toluene-EtOAc 9-1) showed essentially quantitative formation of the enolphosphate intermediate. The reaction mixture was maintained near 0° C. and 3-methoxyphenyl magnesium bromide (250 mL of a 0.74M solution in THF, 0.185 mol) was added by cannula over approximately 5 min. The resulting mixture was stirred at 0° C. for 2 hour, and then it was allowed to warm to 25° C. overnight. By TLC analysis, loss of enolphosphate had accompanied the formation of a major product which migrated at high Rf. The reaction was worked up by pouring it over a large excess of iced NH₄Cl solution, and the crude product was extracted with with ethyl acetate. The organic extracts were washed with brine and dried over anhydrous sodium sulfate. After filtration and removal of the solvents, a brown oil was obtained. The oil was purified by chromatography over silica gel which employed a hexane to chloroform gradient. Pooling and concentration of appropriate fractions gave an amber oil which amounted to 40.3 g (83%): ¹H NMR (CDCl₃) δ 7.85 (d, J=8.6 Hz, 2H) 7.10–7.0 (m, 1H), 6.90–6.70 (m, 6H), 6.70–6.60 (m, 2H), 3.80 (s, 6H), 3.67 (s, 3H), 3.10–2.90 (m, 2H), 2.90–2.70 (m, 2H); MS (FD) m/e 400 (M+); Anal. Calc'd. for C₂₆H₂₄O₄: C, 77.98; H, 6.04; N, 0.00. Found: C, 77.49; H, 6.20; N, 0.00.

Preparation 2A

[3,4-dihydro-6-methoxy-2-(3-[3,4-dihydro-6-methoxy-2-(3-methoxyphenyl)-1-naphthalenyl][4-[2-(1-piperidinyl)ethoxy]phenyl]methanone hydrochloride

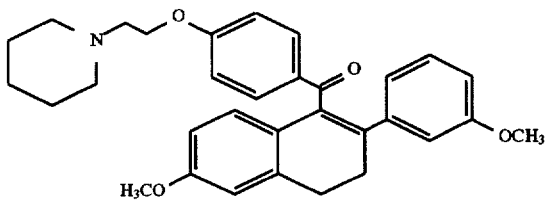

Sodium hydride (60% in mineral oil, 2.68 g, 0.067 mol) was suspended in anhydrous THF (300 mL) under a nitrogen atmosphere and the suspension was cooled to 5° C. in an ice bath. A solution consisting of the compound of Preparation 1A (26.0 g, 0.0638 mol) in a minimum of THF was added dropwise and after the evolution of hydrogen subsided, the mixture was kept cooled and stirred for an hour to complete formation of the enolate. With continued cooling, diphenyl chlorophosphate (17.1 g, 13.2 mL, 0.0638 mol) in THF (75 mL) was added at a rate so that the temperature of the reaction mixture remained below 10° C. Following the completion of the addition, the reaction mixture was allowed to warm to room temperature while stirring was continued. Analysis of a small sample by TLC (SiO₂, Toluene-EtOAc 9-1) showed essentially quantitative formation of the enol phosphate intermediate. The reaction mixture was maintained near 5° C. and 3-methoxyphenyl magnesium bromide (150 mL of a 0.64M solution in THF, 0.096 mol) was added by cannula. The resulting mixture was stirred at 0° C. for 1 hour, and then it was allowed to warm to 25° C. and stirred for one hour longer. The reaction was kept cooled and carefully quenched by gradual addition of 50 mL of 1N sulfuric acid. After adjusting the pH to 7.0, most of the THF was removed under reduced pressure. The aqueous residue was distributed between water and chloroform. The organic layer was washed with brine and dried over anhydrous sodium sulfate. Concentration provided an oil which was purified by chromatography over silica gel which utilized a gradient of chloroform to 95:5 chloroform:methanol to elute the product. Appropriate fractions provided 36 gms of the crude free base which was practically identical to the free base product of Example 5. The free base was dissolved in methanol and treated with an excess of 5N HCl solution, then concentrated to dryness. The residue was recrystallized from methanol-ethyl acetate to provide 27.8 g (82%) of the desired hydrochloride salt: ¹H NMR (DMSO-d₆) d 10.09 (bs, 1H), 7.76 (d, J=8.7 Hz, 1H), 7.11–7.02 (m, 2H), 6.94 (d, J=8.8 Hz, 1H), 6.86 (d, J=1.2 Hz, 1H), 6.81–6.72 (m, 2H), 6.66 (dd, J=8.2 Hz, 2.5, 1H), 6.61 (d, J=3.1 Hz, 1H), 4.37 (t, J=4.6 Hz, 2H), 3.69 (s, 3H), 3.57 (s, 3H), 3.01–2.82 (m, 4H), 2.78–2.63 (m, 2H), 1.81–1.58 (m, 5H), 1.31 (m, 1H); MS (FD) m/e 497 (M+; loss of HCl); Anal. Calc'd. for Anal.

Calc'd. for $C_{32}H_{36}ClNO_4$: C, 71.96; H, 6.79; N, 2.62. Found: C, 71.69; H, 6.77; N, 2.48.

Preparation 3

[3,4-dihydro-6-methoxy-2-(3-methoxyphenyl)-1-naphthalenyl](4-hydroxyphenyl)methanone

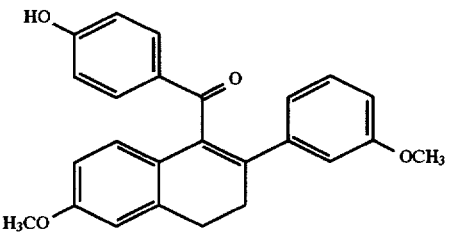

To EtSH (12.5 g, 14.9 mL, 0.20 mol) in anhydrous ethyl ether (300 mL) at −78° C. under a dry nitrogen atmosphere in a 1 L single neck RB flask was added slowly via syringe 1.6M n-BuLi (113 mL, 0.180 mol) over 1 hour. After addition was complete, the ether was removed under vacuum and a solution of [3,4-dihydro-6-methoxy-2-(3-methoxyphenyl)-1-naphthalenyl](4-methoxyphenyl) methanone (24.0 g, 0.065 mol) in anhydrous DMF (150 mL) was added. The reaction mixture was heated at 70°–80° C. for 2.5 hours and then at 65° C. for 20 hr. TLC analysis (SiO$_2$, Toluene-EtOAc 9-1) showed the starting material to be nearly gone. Two spots were present at lower R$_f$. These were attributed to the desired product and the corresponding diphenol (lowest spot). The reaction mixture was allowed to cool and was then poured into 500 mL iced 1N HCl solution. The crude product was extracted into EtOAc. The EtOAc phase was washed with saturated aq. NaCl solution, dried over anhydrous MgSO$_4$, and evaporated to a yellow oil. The product was purified by chromatography over silica gel using a gradient consisting of chloroform changing linearly 95:5 chloroform:methanol. Following evaporation of the appropriate fractions, a yellow oil was obtained which was recrystallized from ethyl ether to yield 21.3 g, (54%) of the desired product, mp 197°–8° C. $^1$H NMR (CDCl$_3$) d 7.76 (d, J=8.6 Hz, 2H), 7.10–7.00 (m, 1H), 6.90–6.70 (m, 4H), 6.70–6.60 (m, 4H), 6.07 (bs, 1H), 3.78 (s, 3H), 3.62 (s, 3H), 3.10–2.90 (m, 2H), 2.90–2.70 (m, 21H); MS (FD) m/e 386 (M+); Anal. Calc'd. for $C_{25}H_{22}O_4$: C, 77.70; H, 5.74. Found: C, 77.45; H, 5.66.

Preparation 4

[3,4-dihydro-6-methoxy-2-(3-methoxyphenyl)-1-naphthalenyl][4-[2-(1-piperdinyl)ethoxy]phenylmethanone]

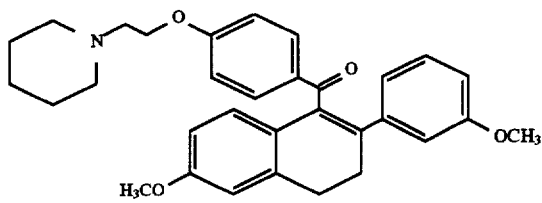

[3,4-dihydro-6-methoxy-2-(3-methoxyphenyl)-1-naphthalenyl](4-hydroxyphenyl)methanone (3.5 g, 9.0 mmol), anhydrous K$_2$CO$_3$ (6.25 g, 45 mmol), N-2-chloroethylpiperidine hydrochloride (1.75 g, 9.5 mmol, Aldrich Chem. Co.) 10 mg of KI, and anhydrous DMF (150 mL) were combined under a nitrogen atmosphere and the resulting mixture was stirred at room temperature for 16 hr. The DMF was removed under reduced pressure and the residue was distributed into water and ethyl acetate. The organic layer was separated, washed with brine and dried over anhydrous sodium sulfate. After concentration to an oil, the product was purified by column chromatography over silica gel using a gradient from chloroform to 95:5 chloroform:methanol. The appropriate fractions gave, on evaporation of the solvent and vacuum drying of the residue at 80° C. overnight, an oil which weighed 3.1 g (69%). $^1$H NMR (CDCl$_3$) d 7.80 (d, J=9.0 Hz, 2H), 7.10–7.00 (m, 1H), 6.90–6.70 (m, 6H), 6.70–6.68 (m, 2H), 4.09 (t, J=5.9 Hz, 2H), 3.78 (s, 3H), 3.65 (s, 3H), 3.02 (t, J=8.1 Hz, 2H), 2.90–2.70 (m, 4H), 2.60–2.40 (m, 3H), 1.70–1.50 (m, 5H), 1.50–1.01 (m, 2H); MS (FD) m/e 497 (M+); Anal. Calc'd. for $C_{32}H_{35}NO_4$: C, 77.24; H, 7.09; N, 2.82. Found: C, 77.05; H, 7.19; N, 3.05.

Preparation 5

[3,4-dihydro-6-methoxy-2-(3-methoxyphenyl)-1-naphthalenyl][4-[2-(1-piperdinyl)ethoxy]phenylmethanol], free base

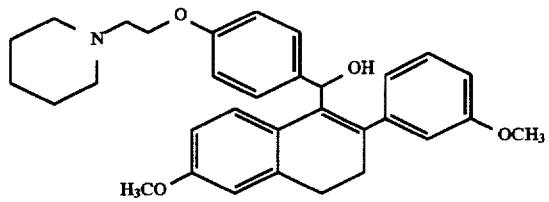

A solution of 6.7 g (13.4 mmol) of [3,4-dihydro-6-methoxy-2-(3-methoxyphenyl)-1-naphthalenyl][4-[2-(1-piperdinyl)ethoxy]phenyl methanone], free base in 200 mL of THF was prepared and 1.02 g (27 mmol) of LiAlH$_4$ was added. The reaction was allowed to proceed at ambient temperature under a nitrogen atmosphere for three hours. The reaction was quenched with the addition of 10 mL of 5N NaOH. The mixture was extracted with ether and the ether layer was washed with brine. The ether solution was dried with anhydrous Na$_2$SO$_4$ and evaporated to dryness. This yielded 6.6 g (98%) of the title compound a tan amorphous powder.

$^1$H NMR (CDCl$_3$) d 7.35 (d, J=8.5 Hz, 2H), 7.25 (d, J=7.3 Hz, 2H), 6.92–6.77 (m, 5H), 6.74 (d, J=2.7 Hz, 1H), 6.52 (dd, J=7.2 Hz, J=2.5 Hz, 1H), 5.85 (s, 1H), 4.20 (t, J=1.3 Hz, 2H), 3.89 (s, 1H), 3.75 (s, 3H), 3.73 (s, 3H), 2.94–2.80 (m, 4H), 2.71–2.50 (m, 6H), 1.77–1.62 (m, 4H), 1.52–1.41 (m, 2H); MS (FD) m/e (M+); Anal. Calc'd. for $C_{32}H_{37}NO_4 \cdot 0.5$ mol H$_2$O: C, 80.14; H, 6.93; N, 2.92. Found: C, 78.66; H, 7.01, N, 2.87.

Example 1A 3,8-methoxy-11-[4-[2-(1-piperidinyl)ethoxy]phenyl]-11H-5,6-dihydrobenzo[a]fluorene, hydrochloride salt

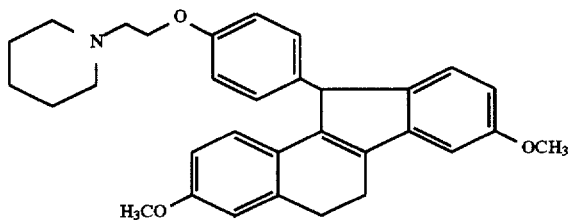

A solution of 43.8 g (0.088 mmol) of [3,4-dihydro-6-methoxy-2-(3-methoxyphenyl)-1-naphthalenyl][4-[2-(1-piperdinyl)ethoxy]phenylmethanone], free base in anhydrous THF (200 mL) was reduced by the addition of lithium aluminum hydride (3.7 g, 0.097 mol) by the procedure of Preparation 5. Following concentration of the ether extract, the [3,4-dihydro-6-methoxy-2-(3-methoxyphenyl)-1-naphthalenyl][4-[2-(1-piperdinyl)ethoxy]phenylmethanol], free base was dissolved in methanol (200 mL) and 1N aqueous hydrochloric acid (200 mL) was added. The resulting solution was stirred and heated at 50° C. for 2 hr. The solution was allowed to cool and stand at ambient temperature for 16 hr during which time a precipitate began to appear. The mixture was concentrated to dryness to provide a residue of 44 g (100%). Analysis by NMR spectroscopy indicated the product to be predominantly the desired material. However, a lesser amount (approx 20%) of another compound was present. To provide a purified sample of the title compound, a 1.1 g portion of the crude product was purified by preparative reversed phase HPLC. Elution with a gradient system consisting initially of 40:60 acetonitrile:0.5% ammonium dihydrogen phosphate buffer and changing to 65:35 acetonitrile:buffer over 40 minutes provided only a partial separation of the two materials. Appropriate fractions were combined and concentrated to remove most of the acetonitrile. The desired product was extracted from the remaining aqueous phase with ethyl acetate. The combined ethyl acetate extracts were dried over anhydrous magnesium sulfate and concentrated, then treated with an excess of HCl in isopropyl alcohol and reconcentrated to provide 108 mg of an oil. Recrystallization from isopropyl alcohol provided 87 mg of the desired product, m.p. 217°-18° C. (decomp).

$^1$H NMR (DMSO-$d_6$) d 10.78 (s, 1H), 7.09 (d, J=7.0 Hz, 2H), 7.03–6.94 (m, 2H), 6.87–6.82 (m, 4H), 6.67–6.57 (m, 2H), 4.87 (s, 1H), 4.40–4.31 (m, 2H), 3.77 (s, 3H), 3.70 (s, 3H), 3.48–3.30 (m, 4H), 3.04–2.85 (m, 5H), 2.66–2.55 (m, 1H), 1.87–1.61 (m, 4H), 1.69–1.54 (m, 1H), 1.41–1.28 (m, 1H).

A satisfactory elemental analysis was obtained.

Example 1B

A solution of 2.6 g (0.0052 mmol) of [3,4-dihydro-6-methoxy-2-(3-methoxyphenyl)-1-naphthalenyl][4-[2-(1-piperdinyl)ethoxy]phenylmethanone], free base in anhydrous THF (500 mL) was reduced at ice bath temperature by the addition of lithium aluminum hydride (0.98 g, 0.026 mol) by the procedure of Preparation 5. Following concentration of the ether extract, the [3,4-dihydro-6-methoxy-2-(3-methoxyphenyl)-1-naphthalenyl][4-[2-(1-piperdinyl)ethoxy]phenylmethanol], free base was dissolved in methanol (50 mL) and 1N aqueous hydrochloric acid (50 mL) was added. The resulting solution was concentrated to dryness to provide a residue. The residue was recrystallized from methanol-isopropyl alcohol to provide 2.1 g (81%) of the desired product.

$^1$H NMR identical to that given above; MS (FD) m/e 482 (MH+ for the free base); Anal. Calc'd. for $C_{32}H_{36}ClNO_3$: C, 74.19; H, 7.00; N, 2.70. Found: C, 73.98; H, 7.01, N, 2.83.

TEST PROCEDURES

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine:xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH 8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17a-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17a-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment in the 4-Day OVX Rat assay:

TABLE 1

| Compound | Dose mg/kg)[a] | Uterine Wt. (% Inc.)[b] | Uterine EPO (Vmax)[c] | Serum Cholesterol (% Dec.)[d] |
|---|---|---|---|---|
| Experiment 1 | | | | |
| $EE_2$[e] | 0.1 | 263.0* | 237.5* | 100.0* |
| Example 1 | 0.01 | 38.6* | 15.7 | 65.8* |
| | 0.1 | 24.5* | 41.3 | 69.9* |
| | 1 | 29.8* | 6.0 | 83.5* |
| Experiment 2 | | | | |
| $EE_2$[e] | 0.1 | 133.1* | 114.0* | 84.9* |
| Example 1 | 0.01 | 38.2* | 3.0 | 28.0* |
| | 0.1 | 43.9* | 16.5 | 74.8* |
| | 1 | 38.3* | 6.0 | 73.9* |

[a]mg/kg PO
[b]Uterine Weight % increase versus the ovariectomized controls
[c]Eosinophil peroxidase, $V_{max}$
[d]Serum cholesterol decrease versus ovariectomized controls
[e]17-a-Ethynyl-estradiol In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents were expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl B-cyclodextrin are orally administered to test animals. Results are reported as percent protection relative to ovariectomy.

We claim:
1. A compound of formula I:

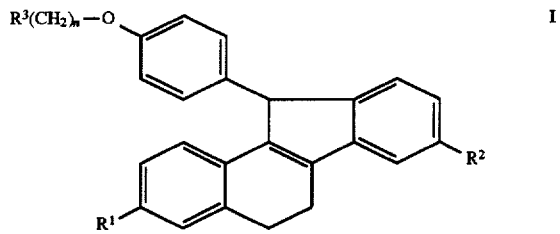

wherein:

$R^1$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, or —OSO$_2$($C_2$-$C_6$ alkyl);

$R^2$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, —OSO$_2$($C_2$-$C_6$ alkyl), or halo;

$R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino; and n is 2 or 3;

or a pharmaceutically acceptable salt or solvate thereof.

2. A compound according to claim 1 wherein n is two.

3. A compound according to claim 1 wherein $R^2$ is methoxy.

4. A compound according to claim 1 wherein $R^2$ is hydroxy.

5. A compound according to claim 1 wherein $R^1$ and $R^2$ are both —OH.

6. A compound according to claim 1 wherein $R^1$ is —H and $R^2$ is —OH.

7. A compound according to claim 1 wherein $R^1$ is —OH and $R^2$ is —H.

8. A compound according to claim 1 wherein $R^1$ and $R^2$ both are —H.

9. A compound according to claim 1 wherein $R^3$ is 1-piperidinyl.

10. A compound according to claim 1 wherein $R^1$ and $R^2$ are both —CH$_3$.

11. A compound according to claim 1 wherein said salt thereof is the hydrochloride salt.

12. A compound according to claim 1 selected from the group consisting of 3,8-dimethoxy-11-[4-[2-(1-piperidinyl)ethoxy]phenyl]-5,6-dihydro-11H-benzo[a]fluorene;

3,8-dihydroxy-11-[4-[2-(1-piperidinyl)ethoxy]phenyl]-5,6-dihydro-11H-benzo[a]fluorene;

3-hydroxy-8-methoxy-11-[4-[2-(1-piperidinyl)ethoxy]phenyl]-5,6-dihydro-11H-benzo[a]fluorene;

3-methoxy-8-hydroxy-11-[4-[2-(1-piperidinyl)ethoxy]phenyl]-5,6-dihydro-11H-benzo[a]fluorene;

3,8,9-trimethoxy-11-[4-[2-(1-piperidinyl)ethoxy]phenyl]-5,6-dihydro-11H-benzo[a]fluorene;

3,8,10-trimethoxy-11-[4-[2-(1-piperidinyl)ethoxy]phenyl]-5,6-dihydro-11H-benzo[a]fluorene;

9-fluoro-3,8-dimethoxy-11-[4-[2-(1-piperidinyl)ethoxy]phenyl]-5,6-dihydro-11H-benzo[a]fluorene;

9-chloro-3,8-dimethoxy-11-[4-[2-(1-piperidinyl)ethoxy]phenyl]-5,6-dihydro-11H-benzo[a]fluorene;

3,8-dimethoxy-9-methyl-11-[4-[2-(1-piperidinyl)ethoxy]phenyl]-5,6-dihydro-11H-benzo[a]fluorene;

3,8-dimethoxy-9-ethyl-11-[4-[2-(1-piperidinyl)ethoxy]phenyl]-5,6-dihydro-11H-benzo[a]fluorene;

8-methoxy-11-[4-[2-(1-piperidinyl)ethoxy]phenyl]-5,6-dihydro-11H-benzo[a]fluorene;

8-hydroxy-11-[4-[2-(1-piperidinyl)ethoxy]phenyl]-5,6-dihydro-11H-benzo[a]fluorene;

8,9-dimethoxy-11-[4-[2-(1-piperidinyl)ethoxy]phenyl]-5,6-dihydro-11H-benzo[a]fluorene;

8,10-dimethoxy-11-[4-[2-(1-piperidinyl)ethoxy]phenyl]-5,6-dihydro-11H-benzo[a]fluorene;

9-fluoro-8-methoxy-11-[4-[2-(1-piperidinyl)ethoxy]phenyl]-5,6-dihydro-11H-benzo[a]fluorene;

9-chloro-8-methoxy-11-[4-[2-(1-piperidinyl)ethoxy]phenyl]-5,6-dihydro-11H-benzo[a]fluorene;

8-methoxy-9-methyl-11-[4-[2-(1-piperidinyl)ethoxy]phenyl]-5,6-dihydro-11H-benzo[a]fluorene;

8-methoxy-9-ethyl-11-[4-[2-(1-piperidinyl)ethoxy]phenyl]-5,6-dihydro-11H-benzo[a]fluorene;

3,8-dimethoxy-11-[4-[2-(1-pyrrolidinyl)ethoxy]phenyl]-5,6-dihydro-11H-benzo[a]fluorene;

3,8-dihydroxy-11-[4-[2-(1-pyrrolidinyl)ethoxy]phenyl]-5,6-dihydro-11H-benzo[a]fluorene;

3-hydroxy-8-methoxy-11-[4-[2-(1-pyrrolidinyl)ethoxy]phenyl]-5,6-dihydro-11H-benzo[a]fluorene;

3-methoxy-8-hydroxy-11-[4-[2-(1-pyrrolidinyl)ethoxy]phenyl]-5,6-dihydro-11H-benzo[a]fluorene;

8-methoxy-11-[4-[2-(1-pyrrolidinyl)ethoxy]phenyl]-5,6-dihydro-11H-benzo[a]fluorene;

8-hydroxy-11-[4-[2-(1-pyrrolidinyl)ethoxy]phenyl]-5,6-dihydro-11H-benzo[a]fluorene;

8,9-dimethoxy-11-[4-[2-(1-pyrrolidinyl)ethoxy]phenyl]-5,6-dihydro-11H-benzo[a]fluorene;

8,10-dimethoxy-11-[4-[2-(1-pyrrolidinyl)ethoxy]phenyl]-5,6-dihydro-11H-benzo[a]fluorene;

3,8-dimethoxy-11-[4-[2-(1-methylpyrrolidinyl)ethoxy]phenyl]-5,6-dihydro-11H-benzo[a]fluorene;

3,8-dihydroxy-11-[4-[2-(1-hexamethyleneimino)ethoxy]phenyl]-5,6-dihydro-11H-benzo[a]fluorene;

3-hydroxy-8-methoxy-11-[4-[2-(1-morpholino)ethoxy]phenyl]-5,6-dihydro-11H-benzo[a]fluorene;

3-methoxy-8-hydroxy-11-[4-[2-(N,N-dimethylamino)ethoxy]phenyl]-5,6-dihydro-11H-benzo[a]fluorene;

3,8,9-trimethoxy-11-[4-[2-(N,N,-diethylamino)ethoxy]phenyl]-5,6-dihydro-11H-benzo[a]fluorene;

3,8,10-trimethoxy-11-[4-[2-(1-methylpyrrolidinyl)ethoxy]phenyl]-5,6-dihydro-11H-benzo[a]fluorene;

9-fluoro-3,8-dimethoxy-11-[4-[2-(N,N-dimethylamino)ethoxy]phenyl]-5,6-dihydro-11H-benzo[a]fluorene;

9-chloro-3,8-dimethoxy-11-[4-[2-(N,N-diisopropylamino)ethoxy]phenyl]-5,6-dihydro-11H-benzo[a]fluorene;

8-methoxy-11-[4-[2-(1-pyrrolidinyl)ethoxy]phenyl]-5,6-dihydro-11H-benzo[a]fluorene;

8-hydroxy-11-[4-[2-(1-methylpyrrolidinyl)ethoxy]phenyl]-5,6-dihydro-11H-benzo[a]fluorene;

8,9-dimethoxy-11-[4-[2-(1-methylpyrrolidinyl)ethoxy]phenyl]-5,6-dihydro-11H-benzo[a]fluorene; and 8,10-dimethoxy-11-[4-[2-(1-methylpyrrolidinyl)ethoxy]phenyl]-5,6-dihydro-11H-benzo[a]fluorene.

13. A pharmaceutical composition comprising a compound according to claim 1, or a pharmaceutically acceptable salt or solvate thereof, in combination with a pharmaceutically acceptable carrier, diluent, or excipient.

14. A compound of formula II

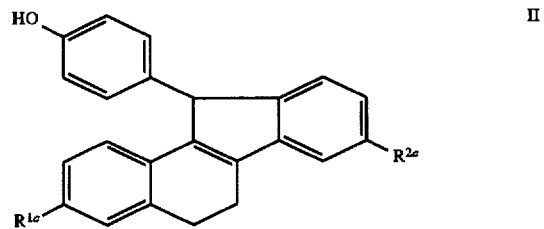

wherein:

$R^{1a}$ is —H or —$OR^5$ in which $R^5$ is a hydroxy protecting group and $R^{2a}$ is —H, halo, or —$OR^6$ in which $R^6$ is a hydroxy protecting group.

15. A method of inhibiting bone loss or bone resorption which comprises administering to a patient in need thereof an effective amount of a compound of claim 1.

16. A method according to claim 15, wherein said bone loss or bone resorption is due to menopause or ovariectomy.

17. A method of lowering serum cholesterol levels which comprises administering to a patient in need thereof an effective amount of a compound of claim 1.

* * * * *